United States Patent [19]

Weil et al.

[11] 4,306,569

[45] Dec. 22, 1981

[54] APPARATUS AND METHOD FOR ASSESSING THE CONDITION OF CRITICALLY ILL PATIENTS

[75] Inventors: Max H. Weil, Beverly Hills; Jose Bisera, Camarillo, both of Calif.

[73] Assignee: Institute of Critical Care Medicine, Los Angeles, Calif.

[21] Appl. No.: 83,296

[22] Filed: Oct. 10, 1979

[51] Int. Cl.³ .............................................. A61B 5/00
[52] U.S. Cl. .................................................... 128/736
[58] Field of Search ........................................ 128/736

[56] References Cited

U.S. PATENT DOCUMENTS

| | | | |
|---|---|---|---|
| 3,781,837 | 12/1973 | Anderson et al. | 128/736 |
| 3,818,895 | 6/1974 | Stewart | 128/736 |
| 3,951,133 | 4/1976 | Reese | 128/736 |
| 3,996,928 | 12/1976 | Marx | 128/736 |
| 4,138,889 | 2/1979 | Fraschini | 128/736 |

Primary Examiner—William E. Kamm
Attorney, Agent, or Firm—Freilich, Hornbaker, Wasserman, Rosen & Fernandez

[57] ABSTRACT

A method and apparatus for assessing the condition of a patient in circulatory shock by measuring the peripheral or skin temperature of the patient, as by measuring the difference between the patient's toe temperature and ambient temperature, which is more accurate than heretofore. The gradient of the toe-minus-ambient temperature difference is calculated, and an indication of poor condition is given if the toe-minus-ambient temperature difference does not rise by at least a predetermined amount such as 3° C. within a predetermined period such as ten hours. Instead of taking only the difference between the temperature at one toe and ambient, the temperatures at both large toes of the patient are taken and the difference between the higher of the two toe temperatures minus ambient is utilized in the calculations that provide an indication of patient condition.

11 Claims, 10 Drawing Figures

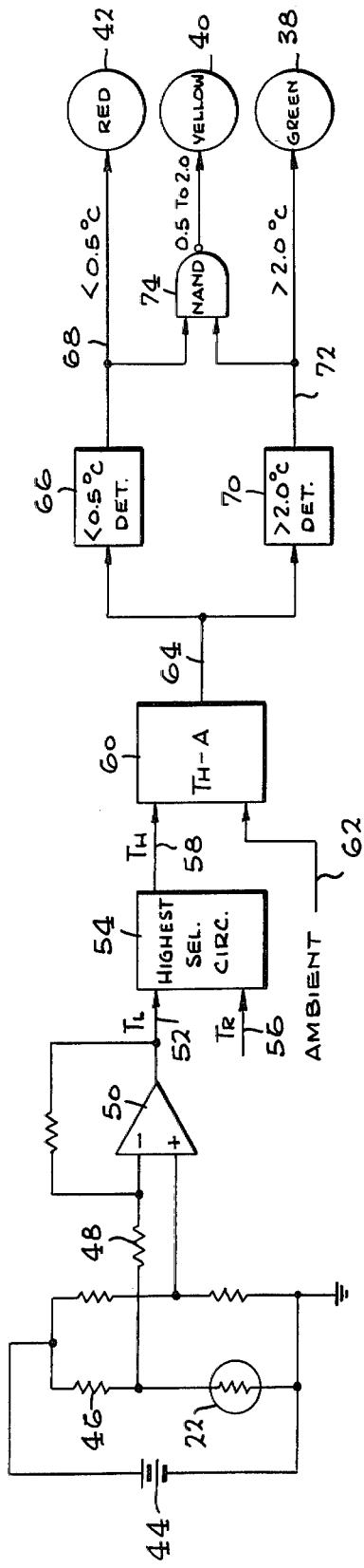
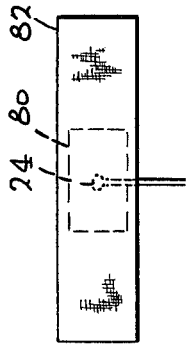
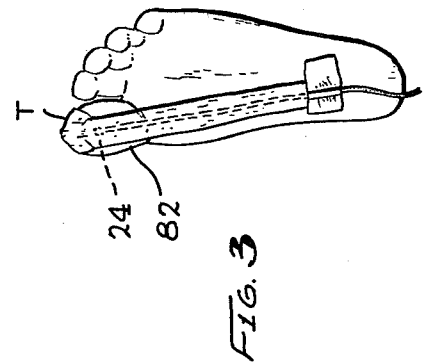
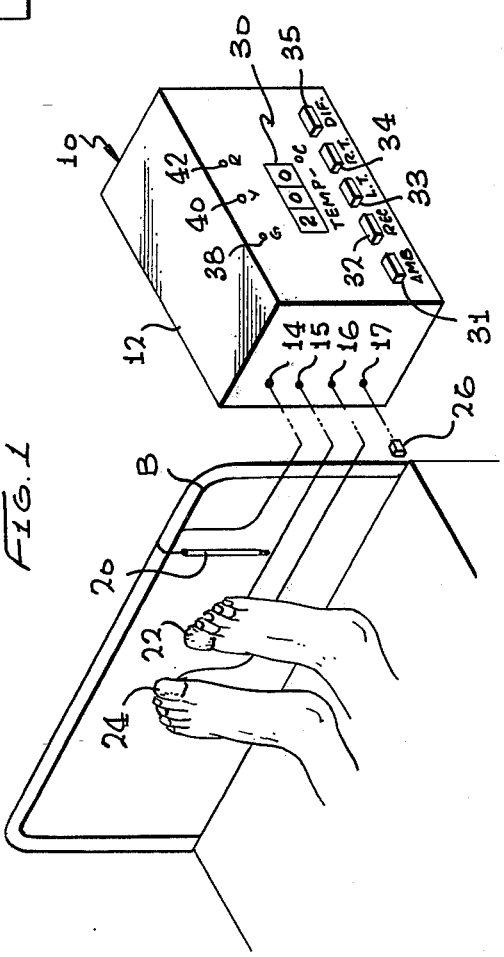

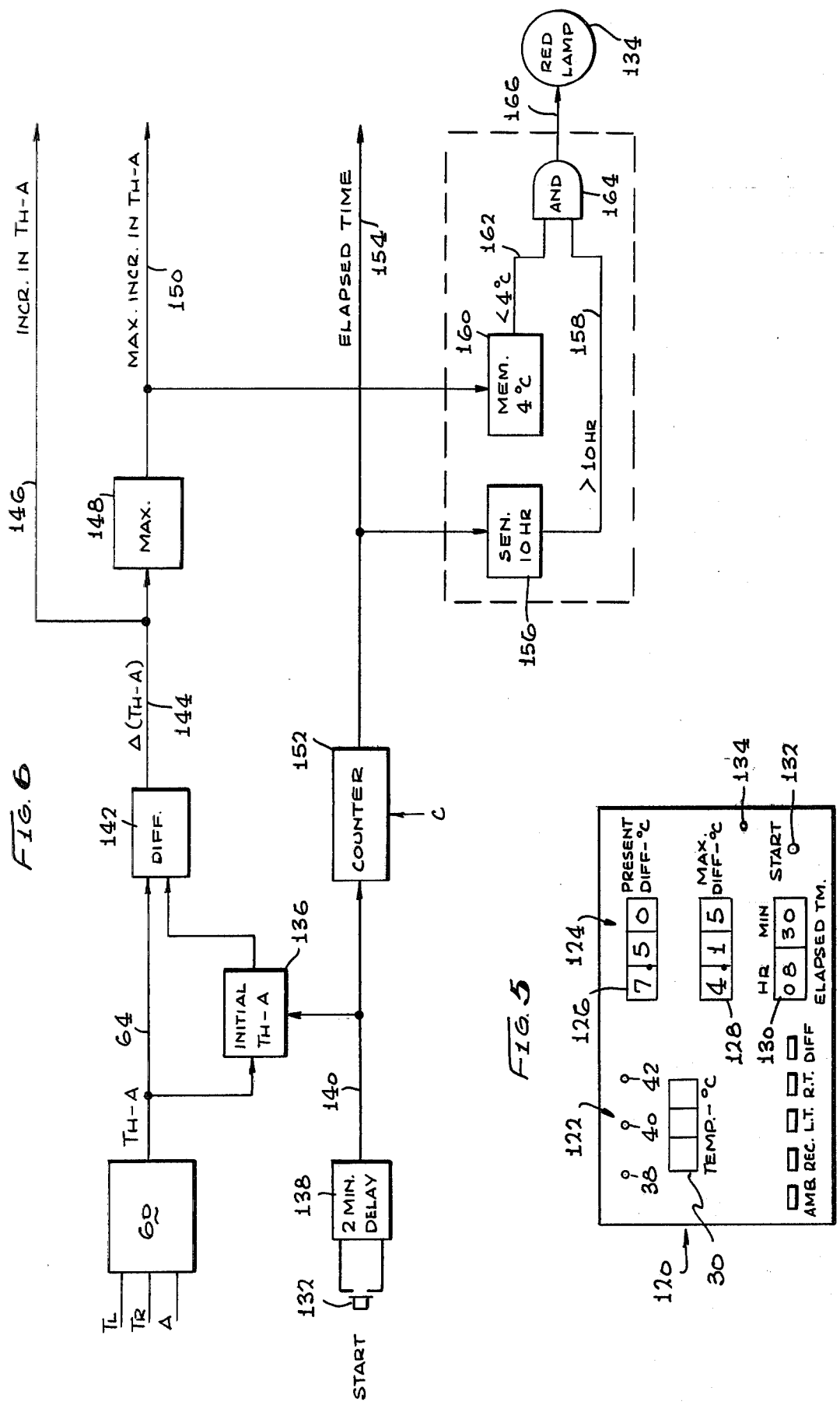

APPARATUS AND METHOD FOR ASSESSING THE CONDITION OF CRITICALLY ILL PATIENTS

BACKGROUND OF THE INVENTION

One of the physical signs of circulatory shock is the loss of warmth in the hands and feet. This results from an inadequacy of blood flow in the extremities. Accordingly, it has been recognized that peripheral skin temperature can provide an indication of blood flow. Studies conducted by the applicant have shown that the peripheral skin temperature, and more particularly the skin temperature taken at a toe of a patient, can provide a good indication of the cardiac output of the patient, and provide a good indication of the likelihood of survival of a critically ill patient suffering from circulatory shock. Furthermore, these studies have shown that a somewhat better accuracy of indication can be obtained by measuring the difference between the toe temperature of the patient and the ambient air temperature. Knowledge about the likelihood of survival of a critically ill patient undergoing circulatory shock, at a time considerably before the appearance of other symptoms indicating this can be useful in determining the treatment to be administered and in assessing the effect of such treatment. A method and apparatus that provided an even more accurate indication of the patient's condition, in a manner that was easily performed and with minimal trauma to the patient, would be of considerable value.

SUMMARY OF THE INVENTION

In accordance with one embodiment of the present invention, an apparatus and method are provided that indicate the physical condition of critically ill patients undergoing circulatory shock, with greater accuracy than heretofore. A method for indicating the physical condition of the patient involves repeatedly measuring the skin temperature at an extremity of the patient such as at a toe. The difference between toe and ambient temperature is repeatedly taken and the gradient of this temperature difference is determined. If this different temperature increases more than a predetermined amount within a predetermined time period, such as more than 4° C. during a predetermined time of several hours, then there is a high probability of patient survival. However, if the temperature difference increases by less than a predetermined amount in a predetermined time period, such as by less than 3° C. during a predetermined period of several hours, then there is a poor chance of patient survival and the apparatus is constructed to then provide an alarm or other indication of poor patient condition. It is found that the gradient of toe-minus-ambient temperature, provides an even better accuracy of prediction of patient survival than measurement of the temperature difference at any given time without regard to the gradient of this temperature difference. The apparatus can be constructed to measure the maximum of change in the temperature difference, and to indicate poor patient condition only when the maximum increase in temperature difference is less than a predetermined amount such as 3° C. within a predetermined period such as ten hours.

Instead of measuring the toe temperature of only one toe of the patient, the temperature at both large toes of the patient is taken, and the temperature difference utilized is that between the highest of the two toe temperatures and ambient temperature. Partial blockage of a region of the circulatory system can result in a relatively low temperature at one leg of the patient, but not at the other. Such blockage, while affecting the temperature of one toe, does not indicate low cardiac output, and therefore the temperature at that toe would not be an accurate indicator of cardiac output of the patient. Accordingly, by taking the higher of the two temperatures for use in determining the toe-minus-ambient temperature difference, a more reliable indication of patient condition can be obtained, either by using this difference or the gradient of this difference.

The novel features of the invention are set forth with particularity in the appended claims. The invention will be best understood from the following description when read in conjunction with the accompanying drawings.

BRIEF DESCRIPTION OF THE DRAWINGS

FIG. 1 is a perspective view of apparatus for indicating the condition of a patient suffering circulatory shock.

FIG. 2 is a schematic diagram of circuitry of the apparatus of FIG. 1.

FIG. 3 is an elevation view showing the manner in which a temperature sensor of the apparatus of FIG. 1 can be applied to a patient.

FIG. 4 is a plan view of the apparatus of FIG. 3.

FIG. 5 is front elevation view of an apparatus for assessing the condition of a patient, which is constructed in accordance with another embodiment of the invention.

FIG. 6 is a schematic diagram showing a portion of the circuitry in the apparatus of FIG. 5.

DESCRIPTION OF THE PREFERRED EMBODIMENTS

Figure 7A:
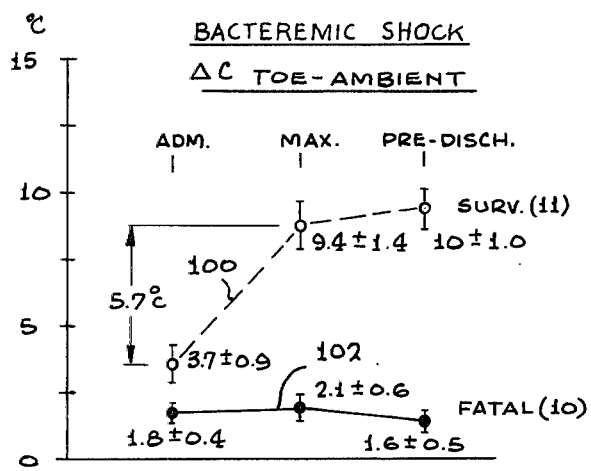
FIGS. 7A–7B are charts showing average measurements of parameters of a group of patients undergoing bacteremic shock.

FIG. 1 illustrates a perfusion indicating apparatus 10 which includes an instrument 12 having four inputs 14–17 connectable to four temperature sensors for obtaining temperature values that can indicate the flow of blood, or profusion, of a patient. The temperature sensors include an ambient temperature sensor 20 which is designed to measure the temperature of the ambient air, and which may include a thermocouple held within a shield that prevents direct contact of the thermocouple with furniture or equipment, and which can be hung over a bed frame B as illustrated. Two other temperature sensors 22,24 are toe temperature sensors designed to measure the skin temperature of the patient at two different locations. A fourth temperature sensor 26 is designed to sense the rectal temperature of the patient, which can be useful in certain diagnosis procedures. The instrument 12 has a readout 30 which is designed to indicate temperature in degrees centigrade. Five different push buttons 31–35 are provided which can be individually depressed to indicate different temperatures on the readout 30. Depressing of the buttons 31–34 causes the readout 30 to respectively indicate the ambient temperature, rectal temperature of the patient, left toe temperature of the patient, or right toe temperature of the patient. Depression of the last button 35 indicates the difference in temperature between the highest of the toe temperatures and ambient temperature. The instruments also include signal lights 38, 40 and 42 of the colors green, yellow, and red that can indicate different states of the patient.

The instrument 12 includes a circuit which energizes the signal lights 38–42 according to the difference between the toe temperature of the patient and ambient temperature. Measurements were taken over a period of years, of patients showing signs of circulatory shock, to try to determine which measurements were good indications of the condition of the patient as by indicating the likelihood of survival of a critically ill patient undergoing circulatory shock. While the cardiac output of such a patient has been found to be a good indication of his physical condition, it is difficult to make direct cardiac output measurements and excessively frequency measurements of this type are detrimental to the patient. Inasmuch as the skin temperature of the patient provides an indication of his cardiac output, measurements were taken at several different skin locations, including the digital pad of the third finger, the large toe, the deltoid region of the arm, the lateral portion of the thigh, and the rectum. It was found that there was a significant correlation between the cardiac output and the temperature of the toe, and the correlation increased somewhat when corrections were made for changes in ambient temperature. Furthermore, it was found that an early measurement of toe temperature could correctly predict a patient outcome (survival or death) in a significant percentage of patients (67 percent).

While the difference between the temperature at a large toe of the patient and ambient temperature can be utilized to predict patient outcome, a somewhat better prediction can be obtained by measuring the temperature of both large toes of the patient, and utilizing the difference between the higher of the two toe temperatures and ambient temperature as the basis for prediction. The temperature at one toe of a patient is determined not only by his cardiac output, but also by the presence of any blockage in his circulatory system, and particularly blockage along any of the smaller arteries along a leg of the patient. In order to help avoid the use in calculations, of a relatively low toe temperature which is due to partial blockage of an artery as opposed to reduced cardiac output, the temperature at both feet of the patient is taken, and particularly at both large toes of the patient. If there is a different between the temperatures at the two large toes, the higher of the temperatures is taken to be the more reliable one inasmuch as it represents the temperature resulting when there is the least circulatory blockage. Accordingly, the instrument 12 is constructed so that when the difference button 35 is depressed, the temperature displayed at the readout 30 is the difference between the higher of the two toe temperatures and ambient temperature.

Studies of many patients have indicated that when the difference temperature (higher of the two toe temperatures minus ambient temperature) is more than about 2° C., there is a high likelihood that the physical state of the patient is good so that he is likely to survive the circulatory shock without heroic measures to aid him. These studies also indicate that when the temperature difference is less than about 0.5° C., there is high likelihood that the patient will expire if heroic measures are not taken. A difference temperature range of 0.5° C. and 2.0° C. indicates that a patient is in an intermediate state which is neither good enough to indicate a high probability of survival nor poor enough to indicate that heroic measures should be considered, but instead that his state should be watched very carefully. The instrument 12 is constructed so that the green light 38 is lit when the difference temperature is more than 2.0° C., the yellow light 40 is lit when the temperature difference is between 0.5° C. and 2.0° C., and the red lamp 42 is lit when the temperature difference is less than 0.5° C.

FIG. 2 illustrates circuitry which is utilized to control the lamps 38–42 of FIG. 1. The circuit shows one toe temperature sensor 22 in the form of a thermistor whose resistance changes with temperature. Currents from a constant voltage source 44 pass in series through a reference resistor 46 and the toe temperature sensor 22, and the divided voltage is passed through another reference resistor 48 to an operational amplifier 50. The output of the amplifier 50, which represents the temperature at the left toe of the patient, is delivered over an input 52 of a highest selecting circuit 54. The circuit 54 also receives a temperature input signal at 56 which represents the temperature at the right toe of the patient. The output 58 of the circuit 54 represents the higher of the two toe temperatures, and this is delivered to a difference calculating circuit 60. The circuit 60 also receives an input over a line 62 representing the ambient temperature, and the circuit 60 delivers an output over line 64 indicating the difference temperature between the higher of the two toe temperatures and ambient temperature. The difference temperature is delivered to a first circuit 66 which detects when the temperature difference is less than 0.5° C., and when this occurs it delivers a signal over line 68 to the red lamp 42 to energize it. The difference temperature on line 64 is also delivered to a circuit 70 that delivers an output on its line 72 when the temperature difference is greater than 2° C. This signal lights the green lamp 38. The outputs from the two detecting circuits 66,70 are also delivered through a NAND gate 74 to the yellow lamp 40, to energize the yellow lamp when the temperature is between 0.5° C. and 2.0° C.

FIGS. 3 and 4 indicate how a toe temperature sensor such as 24 can be attached to the toe T of a patient. The thermistor probe 24 is covered with a polyethylene sheet 80 which is attached to a strip of water proof tape 82. The tape is sealed to the skin to prevent local loss of heat, and to maintain a moisture saturated environment for the probe, to maintain good thermal contact with the skin of the patient while avoiding evaporation of moisture that could lower the temperature.

Figure 8:
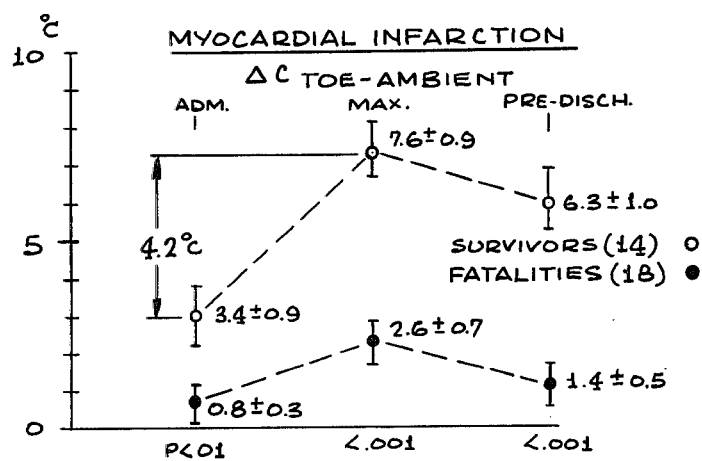
FIG. 8 is a chart showing the variation in toe-minus-ambient temperature of a group of patients undergoing myocardial infarction.
Figure 9:
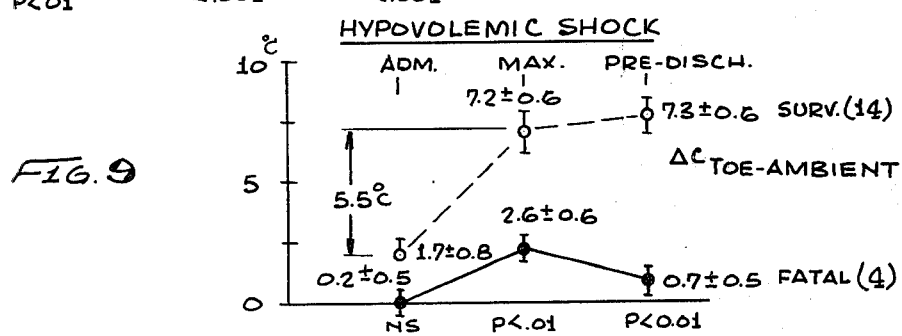
FIG. 9 is a chart showing the variation in toe-minus-ambient temperature of a group of patients undergoing hypovolemic shock.

While measurement of the temperature difference between the toe and ambient temperature of the patient can provide a good indication of the condition of a patient suffering circulatory shock, it has been found that an even better indication of the likelihood of survival of the patient can be obtained by measuring the gradient of the temperature difference. FIGS. 7–9 illustrate parameters measured for on seventy-one critically ill patients suffering circulatory shock and showing the differences in measurements of those patients who expired as compared to those who survived. Of the seventy-one critically ill patients, thirty-two patients suffered from acute myocardial infarction, twenty-one patients from primary bacteremia as indicated by the presence of bacteria in blood samples, and eighteen patients from primary hypovolemia which followed acute blood loss.

Measurements of various parameters were taken throughout the critical period of treatment.

Figure 7B:
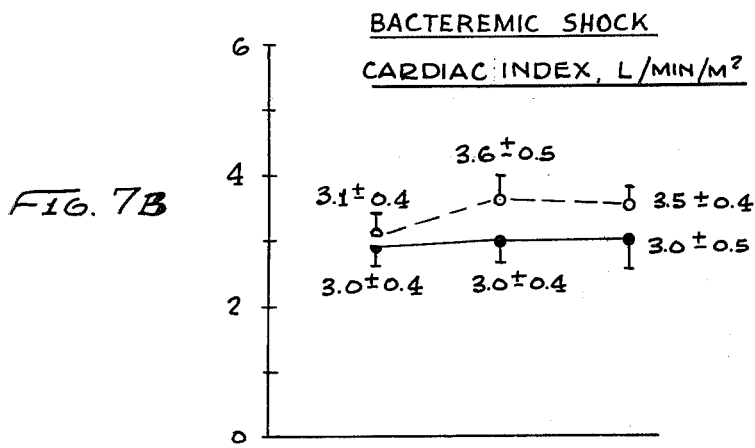

FIG. 7A shows the toe-minus-ambient temperature for patients undergoing bacteremic shock, with the graph 100 showing the characteristics of eleven surviving patients and graph 102 showing the characteristics of 10 patients who expired during an average treatment interval of 25 hours. The temperature difference upon admission was 3.7° C. for those patients who survived and 1.8° C. for those patients who eventually expired. During a period of 14 hours following admission, the maximum temperature difference was 9.4° C. for the survivors and 2.1° C. for those who eventually expired, the 14-hour period being significant in that the maximum temperature differences occurred during this period. The average temperatures of the patients 3 hours prior to discharge of survivors or onset of the agonal phase for those who expired, is also shown. It can be seen that the maximum temperature difference increase of 5.7° C. for the surviving patients is significantly greater than the average maximum increase of only 0.3° C. for those who expired. The temperature difference was taken at intervals of 15 minutes during the treatment period. FIG. 7B shows the average cardiac index in liters per minute per cubic meter for the survivors and fatalities, at these three times, (cardiac index was measured at intervals of four hours) showing the correspondence between temperature difference and cardiac index.

FIG. 8 shows the gradient in temperature difference for a group of thirty-two patients showing symptoms of myocardial infarction. The maximum change in toe-minus-ambient temperature difference was taken during a period of 16 hours after admission. It can be seen that the survivors experienced a maximum increase in temperature difference of 4.2° C. while those who eventually expired experienced a temperature increase of only 1.8° C. during the initial 16-hour period. The survivors showed a decrease in temperature difference after the 16 hours initial period. The expiring patients expired at an average interval of 28 hours following admission to the special study unit.

FIG. 9 shows the temperature difference characteristic for eighteen patients undergoing hypovolemic shock, and showing the maximum increase in toe-minus-ambient temperature difference during a 14-hours period following admission. It can be seen that the fourteen surviving patients showed a maximum increase in temperature difference of 5.5° C. during the 14-hours period, while the fatalities showed an increase of only 2.4° C. A study of the results shows that the toe-minus-ambient temperature typically increased between 4° C. and 6° C. in patients who responded to treatment and recovered, during a period of several hours after admission. However, when the toe-minus-ambient temperature gradient difference increased less than 3° C. over an interval of 12 hours, a fatal outcome was likely. By measuring not only the toe-minus-ambient temperature, but its gradient, the physical condition of patients undergoing circulatory shock can be assessed, and can help indicate what type of treatment to administer.

FIGS. 5 and 6 show an instrument 120 which can be utilized to indicate the temperature gradient of a patient, and also to signal when a poor patient condition is indicated which is likely to be fatal. The instrument has a left portion 122 which is similar to the instrument 12 of FIG. 1 that can indicate different temperature as well as the toe-minus-ambient temperature difference, and also includes another portion 124 which can indicate temperature gradient.

The portion 124 of the instrument has a first read-out 126 which constantly indicates the present temperature difference, which is the difference between the highest of the two toe-temperature sensors and the ambient temperature. Another read-out 128 indicates the maximum change in the temperature difference from the beginning of a test period. Another read-out 130 indicates the elapsed time from the beginning of the test read-out. A button 132 can be depressed to begin the test period (at which time the maximum change in temperature difference on read-out 128 is zero and the elapsed period on read-out 130 is also zero). A warning lamp 134 flashes a warning when the maximum temperature difference is less than a predetermined amount such as less than 3° C. after a predetermined elapsed time such as 10 hours.

FIG. 6 illustrates the circuitry which provides the temperature gradient read out in the instrument of FIG. 5. A circuit 60 similar to that of FIG. 2, produces an output 64 representing the temperature difference at any given time (the highest of the two toe temperatures, represented as $T_H$, minus ambient temperature represented as A). This temperature difference $T_H$-A is stored in a memory 136 at substantially the beginning of the test period, when an operator depresses the start button 132. A two-minute delay period is counted by a timer 138, to deliver a pulse over line 140 two minutes after the start button 132 is depressed, to provide time for all temperature sensors to reach the temperature of the skin or the ambient air. A pulse is then delivered to the memory 136 to record the initial temperature difference. A circuit 142 measures the change in toe-minus-ambient temperature at any given time with respect to the initial time as recorded in the memory 136, and delivers a signal on its output 144 which indicates the increment in toe-minus-ambient temperature. This increment, $\Delta(T_H$-A), is delivered over line 146 to the display 126 of FIG. 5.

The maximum value of the increment, $\Delta(T_H$-A), on line 144 is recorded in a memory 148, and this value is delivered over line 150 to the maximum difference read-out 128 of FIG. 5. The elapsed time from the beginning of the test period, which began soon after the start button 132 was depressed, is counted by a counter 152, and this count is delivered over a line 154 which energizes the elapsed time read-out 130 of FIG. 5. The count of the counter 142 is also delivered to a 10-hour sensing circuit 156 which delivers a pulse over a line 158 when the elapsed time is more than 10 hours. Another circuit 160 delivers a signal over a line 162 when the maximum increment in toe-minus-ambient temperature is less than 3° C. The two lines 158, 162 are connected to an AND gate 164. The AND gate 164 delivers a signal on line 166 to energize the red lamp 134, if the maximum increase in toe-minus-ambient temperature was less than 3° C. after a 10-hour interval following the start of the test period. Thus, the circuit provides an indication of the maximum increase in toe-minus-ambient temperature, and also provides an alarm signal if this maximum increase in temperature is less than a predetermined amount such as 3° C. during a period of several hours such as 10 hours following the beginning of a test which may be started immediately after patient admittance. As discussed above, an increase in toe-minus-ambient temperature of less than about 3° C. during a period of several hours following admission, can indicate very poor patient condition and the likelihood of fatality, so that heroic measures may be indicated.

The precise temperature and time period to utilize in the circuit of FIG. 6 for generating an unfavorable condition-indicating signal, can be made variable, so as to enable a more accurate indication for patients suffering from different illnesses and in different apparent conditions as measured by other symptoms. For example, it may be found desirable to generate a warning if the temperature rise is less than 4° C. in a predetermined period. If the patient has partially recovered prior to admission, so that his toe-minus-ambient temperature is high and is expected to rise only slightly thereafter even if he continues to recover, then the circuit can be constructed to block an alarm signal regardless of temperature gradient, if the toe-minus-ambient temperature exceeds a predetermined level such as 6° C. The circuit also can be constructed to generate a favorable condition-indicating signal if the temperature gradient is more than a certain level such as over 4° C. during a period of 10 hours.

Thus, the invention provides apparatus for assessing the condition of patients undergoing circulatory shock, and especially those who are critically ill. The apparatus can provide an indication of the physical state of the patient, and one which is related to the cardiac output or blood flow from the heart of the patient, by measuring the skin temperature at an extremity of the patient and particularly at his feet, to provide an indication based on a function of the skin temperature such as the toe temperature minus ambient temperature. The effects of partial arterial blockage can be avoided by measuring the toe or other skin temperature at both feet of the patient, and by providing an indication dependent on the higher of the two toe temperatures, such as a readout equal to the higher of the two toe temperatures minus ambient temperature. While the toe-minus-ambient temperature can be utilized to indicate the patient's physical condition, an even better indication can be obtained by determining the gradient of the patient's skin temperature such as of his toe-minus-ambient temperature. A measurement of the gradient in toe-minus-ambient temperature can be taken, and a warning can be signaled if the increase in toe-minus-ambient temperature is less than a predetermined amount such as less than 4° C. during a period of several hours such as 10 hours.

Although particular embodiments of the invention have been described and illustrated herein, it is recognized that modifications and variations may readily occur to those skilled in the art, and consequently, it is intended that the claims be interpreted to cover such modifications and equivalents.

We claim:

1. Apparatus for indicating the condition of a patient who appears to be suffering from circulatory shock, comprising:

skin temperature sensor means for sensing skin temperature;

ambient temperature sensor means for sensing ambient temperature;

circuit means connected to said skin and ambient sensor means, for generating a signal representing the difference between the temperatures sensed by them; and means responsive to said circuit means for generating a signal indicating the physical condition of a patient;

said skin temperature sensor means including a pair of separate skin temperature sensors which each independently senses a skin temperature; and said circuit means being constructed to generate a signal which represents the difference between the higher one of the temperatures sensed by said pair of skin temperature sensors and the temperature sensed by said ambient temperature sensing means.

2. The apparatus described in claim 1 wherein:

said means for indicating the physical condition of a patient includes means for generating a signal indicating an unfavorable condition when the temperature difference between said skin and ambient sensor means increases at less than a predetermined rate with time.

3. The apparatus described in claim 2 wherein:

said means for indicating is constructed to generate said signal indicating an unfavorable condition when the increase in temperature difference is less than about four degrees centigrade during a predetermined period which is a plurality of hours long.

4. Apparatus for indicating the condition of a patient who appears to be suffering from circulatory shock, comprising:

means for generating a first signal representing the temperature of the patient;

means responsive to said first signal for generating a second signal indicating an unfavorable condition of the patient when the temperature of the patient does not rise more than a predetermined amount during a period which is more than one hour.

5. The apparatus described in claim 4 wherein:

said means for generating a signal includes a pair of toe temperature sensor constructed for attachment to the two large toes of a person, an ambient temperature sensor constructed to measure ambient air temperature, and a circuit which generates said first signal wherein said first signal represents the difference between the highest of the temperatures sensed by said pair of toe temperature sensors and the temperature sensed by said ambient temperature sensor.

6. The apparatus described in claim 4 wherein:

said means for generating a second signal generates said second signal when the temperature of the patient represented by said first signal, rises at a rate of less than about three degrees centigrade in said period, and generates a third signal indicating a favorable condition of the patient when the temperature rise is more than about four degrees centigrade in said period.

7. A method for sensing the condition of a patient who appears to be suffering from circulatory shock, comprising:

measuring the skin temperature of the patient at locations on each of his feet;

measuring the ambient temperature; and generating a signal indicating poor patient condition when the temperature difference between the highest of the two feet location and ambient temperature is below a predetermined level.

8. The method described in claim 7 wherein:

said step of generating includes generating a signal indicating poor patient condition when the temperature difference does not rise by at least a predetermined amount of about four degrees centigrade during a predetermined period which is at least one hour long.

9. A method for sensing the condition of a patient who appears to be suffering from circulatory shock, comprising:

measuring the skin temperature of the patient; and generating a signal indicating poor patient condition when said skin temperature does not rise at least at a predetermined temperature-time rate.

10. The method described in claim 9 wherein:

said step of measuring includes measuring the skin temperature of the patient at locations on each of his feet and measuring the ambient temperature; and said step of generating includes generating a signal indicating poor patient condition when the temperature difference between the highest of the two feet locations and ambient temperature does not rise by at least a predetermined rate.

11. A method for sensing the condition of a patient who appears to be suffering from circulatory shock, comprising:

measuring the skin temperature of the patient;

measuring elapsed time;

generating a signal representing a rate of skin temperature rise with time; and generating a signal indicating poor patient condition when the rate of skin temperature rise with time does not at least equal a predetermined rate.

* * * * *